United States Patent
Doughty (10) Patent No.: US 7,309,842 B1
(45) Date of Patent: Dec. 18, 2007

(54) SHIELDED MONOLITHIC MICROPLASMA SOURCE FOR PREVENTION OF CONTINUOUS THIN FILM FORMATION

(75) Inventor: Frank C. Doughty, North Andover, MA (US)

(73) Assignee: Verionix Incorporated, North Andover, MA (US)

( * ) Notice: Subject to any disclaimer, the term of this patent is extended or adjusted under 35 U.S.C. 154(b) by 0 days.

(21) Appl. No.: 10/907,024

(22) Filed: Mar. 16, 2005

Related U.S. Application Data (60) Provisional application No. 60/554,850, filed on Mar. 19, 2004.

(51) Int. Cl.
*C23F 13/00* (2006.01)
*C23C 14/04* (2006.01)

(52) U.S. Cl. ............... 219/121.43; 219/121.36; 219/121.44; 219/121.47; 219/121.59; 118/723 R; 118/723 E; 156/345.35; 156/345.48; 204/298.11; 204/298.08

(58) Field of Classification Search ........... 219/121.43, 219/121.36, 121.47, 121.59, 121.44; 204/298.03, 204/298.11, 298.08, 296.19; 118/723 R, 118/723 E; 156/345.35, 345.48
See application file for complete search history.

(56) References Cited

U.S. PATENT DOCUMENTS

| | | |
|---|---|---|
| 4,575,241 A | 3/1986 | Demers et al. |
| 4,664,477 A | 5/1987 | Andrieu et al. |
| 4,820,048 A | 4/1989 | Barnard |
| 4,888,597 A * | 12/1989 | Rebiez et al. ............... 343/778 |
| 4,918,031 A | 4/1990 | Flamm et al. |
| 4,973,159 A | 11/1990 | Sohma et al. |
| 5,234,529 A | 8/1993 | Johnson |
| 5,483,337 A | 1/1996 | Barnard et al. |
| 5,526,172 A * | 6/1996 | Kanack ................... 359/291 |
| 5,570,179 A | 10/1996 | Weckstrom |

(Continued)

FOREIGN PATENT DOCUMENTS

JP    2003234333 A  *  8/2003

OTHER PUBLICATIONS

Gaurand, et al., An Innovative Plasma Source For On Line Process Monitoring, Alcatel Vacuum Technology France, Annecy, France.

(Continued)

*Primary Examiner*—Tu Ba Hoang
*Assistant Examiner*—Stephen J. Ralis
(74) *Attorney, Agent, or Firm*—Kurt Rauschenbach; Rauschenbach Patent Law Group, LLC (57) ABSTRACT

A monolithic microplasma source includes a dielectric substrate having an outer surface that is exposed to a time varying electric field. A gap layer is positioned on an inner surface of the dielectric substrate. A shield including a slit is positioned on the gap layer. A relief structure is formed in at least one of the gap layer and the dielectric substrate. The dimensions of the gap layer, the slit in the shield, and the relief structure are chosen so as to prevent a formation of a continuous film across the relief structure. A chamber containing a gas is positioned adjacent to the shield so that the gas is ionized to form a microplasma when an electric field is induced in the chamber by the incident time varying electric field.

27 Claims, 5 Drawing Sheets

U.S. PATENT DOCUMENTS

| | | | |
|---|---|---|---|
| 5,596,407 A | 1/1997 | Zander et al. | |
| 5,654,796 A | 8/1997 | Mundt | |
| 5,942,855 A | 8/1999 | Hopwood | |
| 5,982,334 A * | 11/1999 | Manasson et al. | 343/785 |
| 5,986,747 A | 11/1999 | Moran | |
| 6,043,881 A | 3/2000 | Wegrzyn et al. | |
| 6,048,798 A * | 4/2000 | Gadgil et al. | 438/714 |
| 6,132,566 A | 10/2000 | Hofmann et al. | 204/192.17 |
| 6,313,803 B1 * | 11/2001 | Manasson et al. | 343/756 |
| 6,359,250 B1 * | 3/2002 | Blonigan et al. | 219/121.43 |
| 6,381,014 B1 | 4/2002 | Platzer et al. | |
| 6,388,632 B1 * | 5/2002 | Murakawa et al. | 343/770 |
| 6,429,935 B1 | 8/2002 | Duan | |
| 6,459,066 B1 * | 10/2002 | Khater et al. | 219/121.41 |
| 6,523,493 B1 * | 2/2003 | Brcka | 118/723 I |
| 6,538,734 B2 | 3/2003 | Powell | |
| 6,565,717 B1 | 5/2003 | Leet et al. | |
| 6,577,390 B1 | 6/2003 | Efthimion | |
| 6,594,010 B2 | 7/2003 | Malczweski et al. | |
| 6,643,014 B2 | 11/2003 | Chevalier et al. | |
| 6,685,799 B2 | 2/2004 | Davis et al. | |
| 6,738,600 B1 * | 5/2004 | Newton et al. | 455/66.1 |
| 6,815,739 B2 * | 11/2004 | Huff et al. | 257/275 |
| 6,835,949 B2 * | 12/2004 | Weiss et al. | 257/21 |
| 6,914,005 B2 * | 7/2005 | Furuse et al. | 438/706 |
| 6,917,165 B2 | 7/2005 | Hopwood et al. | |
| 6,953,908 B2 * | 10/2005 | Ishii et al. | 219/121.43 |
| 2002/0071117 A1 | 6/2002 | Ukon et al. | |
| 2002/0092618 A1 * | 7/2002 | Collins | 156/345.48 |
| 2002/0093652 A1 | 7/2002 | Powell | |
| 2003/0080685 A1 * | 5/2003 | Grotjohn et al. | 315/111.21 |
| 2003/0128919 A1 * | 7/2003 | Weiss et al. | 385/25 |
| 2003/0214651 A1 | 11/2003 | Hudak | |
| 2004/0164682 A1 | 8/2004 | Hopwood et al. | |
| 2005/0098117 A1 * | 5/2005 | DiVergilio et al. | 118/723 E |
| 2005/0205532 A1 * | 9/2005 | Patrick et al. | 219/121.43 |
| 2005/0222781 A1 * | 10/2005 | Yue et al. | 702/30 |

OTHER PUBLICATIONS

Messier, et al., Miniaturization Of Inductively Coupled Plasma Sources, Department of Electrical and Computer Engineering, Northeastern University, Boston, MA, USA.

Hopwood, et al., Fabrication And Characterization Of A Micromachined 5mm Inductively Coupled Plasma Generator, J. Vac. Sci. Technol. B, Sep./Oct. 2000, pp. 2446-2451, vol. 18, No. 5.

Johnson, et al., High-Density Plasma Sources, Noyes, 1995.

Doughty. Microplasma Emission Spectrometer, U.S. Appl. No. 10/708,450, filed Mar. 4, 2004.

Hopwood, A Microfabricated Inductively-Coupled Plasma Generator, pp. 1-17, Department of Electrical and Computer Engineering, Northeastern University, Boston, MA, USA.

* cited by examiner

| Shield # | Widths | | Open Fraction | Number Lines | Edge Length mm |
|---|---|---|---|---|---|
| | Shield (microns) | Slot (microns) | | | |
| none | none | infinite | 1.00 | 0 | infinite |
| 1 | 720 | 495 | 0.41 | 4x3 | 176 |
| 2 | 472 | 252 | 0.35 | 4x5 | 216 |
| 3 | 351 | 135 | 0.28 | 4x8 | 384 |
| 4 | 230 | 252 | 0.52 | 4x8 | 376 |

SHIELDED MONOLITHIC MICROPLASMA SOURCE FOR PREVENTION OF CONTINUOUS THIN FILM FORMATION

RELATED APPLICATION SECTION

This application is a non-provisional patent application of U.S. Provisional Patent Application Ser. No. 60/554,850, filed Mar. 19, 2004, entitled "A Shielded Microplasma Source and an Emission Spectrometer Using a Shielded Microplasma Source", the entire application of which is incorporated herein by reference.

FEDERAL RESEARCH STATEMENT

This application was made, in part, with the United States Government support from National Science Foundation, Program SBIR Phase I and DMII SBIR, under Grant Contract Number 0319494. The Government may have certain rights in the claimed invention.

INTRODUCTION

The section headings used herein are for organizational purposes only and should not to be construed as limiting the subject matter described in the present application.

The present invention relates to microplasma sources and to systems that use microplasma sources. Microplasma sources generate relatively small volume microplasmas that are on order of a few cubic centimeters or less. Known microplasma sources inductively couple electric and magnetic fields with a high efficiency resonant antenna structure. See, for example, Hopwood, J. Vac. Sci. Technol. B, 18.5, September/October 2000, pg. 2446.

There are many applications for microplasmas. For example, microplasmas can be used in spectrometer systems that perform portable chemical analysis. Microplasmas can also be used for portable sterilization systems.

BRIEF DESCRIPTION OF THE DRAWINGS

The aspects of this invention may be better understood by referring to the following description in conjunction with the accompanying drawings, in which like numerals indicate like structural elements and features in various figures. The drawings are not necessarily to scale. The skilled artisan will understand that the drawings, described below, are for illustration purposes only. The drawings are not intended to limit the scope of the present teachings in any way.

DETAILED DESCRIPTION

While the present teachings are described in conjunction with various embodiments and examples, it is not intended that the present teachings be limited to such embodiments. On the contrary, the present teachings encompass various alternatives, modifications and equivalents, as will be appreciated by those of skill in the art.

It should be understood that the individual steps of the methods of the present invention may be performed in any order and/or simultaneously as long as the invention remains operable. Furthermore, it should be understood that the apparatus and methods of the present invention can include any number or all of the described embodiments as long as the invention remains operable.

Some aspects of the microplasma source of the present invention are described in connection with a monolithic microplasma source. However, it is understood that the microplasma source of the present invention can be constructed as a monolithic device or as a hybrid device. In addition, aspects of the microplasma source of the present invention are described in connection with a microplasma emission spectrometer. However, it is understood that the microplasma source can be used in many apparatus and has numerous applications.

The microplasma source of the present invention includes a shield. Shields are used in some known plasma sources to prevent the deposition of conductive materials on windows or inductive coils that are exposed to the plasma. These shields cause unwanted capacitive coupling. Some known plasma sources include machined slot structures in the shield that induce additional inductive coupling. These known plasma sources have relatively low capacitive coupling from the non-resonant antenna used to generate the plasma and thus have relatively low plasma potential. Decreasing the plasma potential is desirable for certain processes. See, for example, Johnson and Popov, "High-Density Plasma Sources, Noyes, 1995. The shield slot structures have lateral dimensions along the long axis of the slot that are typically more than 100 mm and have slot width dimensions across the gap that are at least 1-2 mm. The shield slot structures are typically made using conventional machining techniques.

In these known plasma sources, the slot areas are typically much less than the surface area of the plasma. The area-to-volume ratio and the sheath-to-volume ratio of the plasmas generated by these sources are typically very low. Antenna structures are used to induce electric fields across the slots. The antenna structures are typically separated from the shield by a gap that is between a few millimeters and a few centimeters wide.

When dielectric substrates are used to form the gap between the antenna structure and the shield, the dielectric substrate must have a sufficient thickness to provide enough mechanical strength to support the vacuum loads experienced during operation. In many plasma generators, the thickness of the dielectric window will be at least a centimeter thick. The parasitic capacitance of the shield is usually insignificant. Consequently, the shield does not appreciably change the operating parameters of the plasma sources operating in a non-resonant mode.

Typically the shield is metallic and is mechanically attached to the chamber wall with bolts. The slot area relative to the shield area is relatively low, typically much less 2 and can be as low as 1%. Power coupling is relatively efficient because the effective plasma resistance, $R_p$, as seen by the antenna is relatively high compared with the antenna resistance. See, for example, Hopwood, J. Vac. Sci. Technol.

B, Vol. 18, No. 5, September/October 2000, pg 2451). Thus, low slot areas are acceptable, and the structure is mechanically self-supporting.

A microplasma is a very small-scale plasma that has dimensions that are in the range of 0.1 to 5 cm. Microplasma sources inductively couple electric and magnetic fields with a high efficiency resonant antenna structure. The electric and magnetic fields induce currents in the microplasma. The induced current results in electron excitation and the creation of ions and electrons that sustain the plasma discharge. Some microplasma sources use resonant antenna structures that are driven at 100 MHz or higher.

Known microplasma sources do not include shields. Microplasmas are not just small scale versions of conventional plasmas. In fact, microplasmas are fundamentally different from conventional plasmas. For example, inductively coupled microplasmas have a plasma resistive impedance that is greater than the inductive impedance, $Rp>>\omega Lp$. This is in contrast to conventional plasmas that have plasma resistive impedances that are less than the inductive impedance, $Rp<<\omega Lp$. Plasma volume scales with the plasma length cubed, while the sheath width is determined primarily by the plasma density and by the electron temperature and is somewhat independent of the dimensions of the plasma. Thus, the sheath width does not scale appreciably with the size of the plasma. In addition, the coupling characteristics of microplasmas are different from the coupling characteristics of conventional plasma sources. Furthermore, the ratio, Rsp, of sheath volume to plasma volume is $Rsp<<1$ for conventional plasmas, but can be much larger for microplasmas.

It is not known in the art whether microplasma sources can operate with shields and to what extent including a shield affects the operating characteristics of a microplasma source. The Applicant has discovered that microplasma sources can operate efficiently with a shield and that the use of a shield can greatly increase the lifetime of a microplasma source. In addition, the Applicant has discovered various shield geometries that are particularly suitable for microplasma sources.

The microplasma source of the present invention includes a shield that protects the source from materials generated by the plasma. The shield prevents the deposition of a continuous conducting coating with sufficient thickness and conductivity to decouple the electromagnetic energy transfer from the power source to the plasma.

Figure 1:
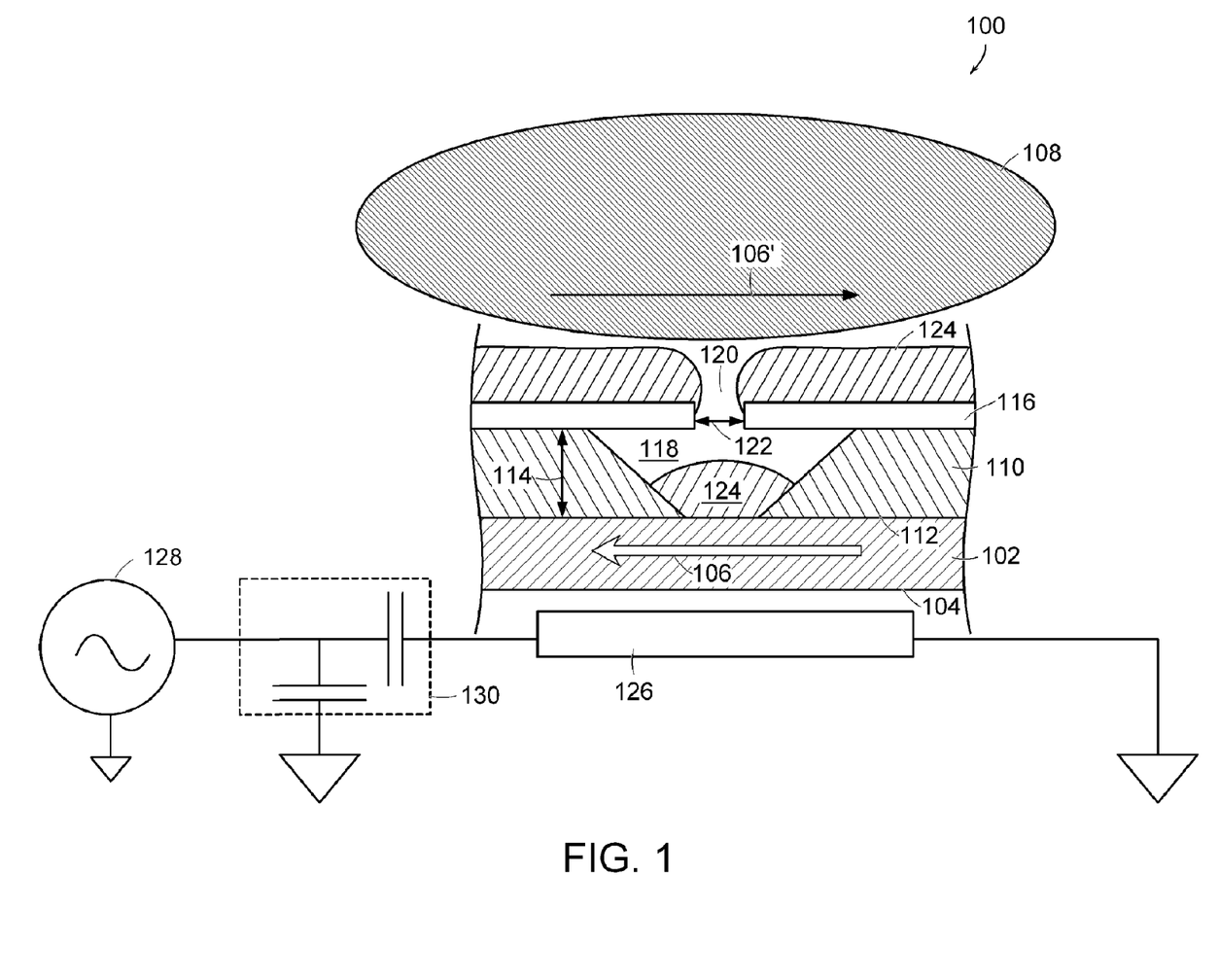
FIG. 1 illustrates a cross sectional view of an embodiment of a single slit of a shielded microplasma source according to the present invention.

FIG. 1 illustrates a cross sectional view of an embodiment of a single slit of a shielded microplasma source 100 according to the present invention. The microplasma source 100 includes a dielectric substrate 102. In one embodiment, the dielectric substrate 102 is a substantially planar dielectric substrate. In another embodiment, the dielectric substrate 102 has a convex or concave curvature on at least one surface. Any type of dielectric substrate can be used. For example, the dielectric substrate 102 can be formed of materials such as quartz, sapphire, glass, alumina, aluminum nitride, or a polymeric material. One skilled in the art will appreciate that numerous other types of dielectric substrates can be used. In some embodiments, the dielectric substrate 102 forms a mechanical support for the microplasma source 100.

The outer surface 104 of the dielectric substrate 102 forms a vacuum or pressure window on a chamber or vessel (not shown) that contains the microplasma. The outer surface 104 of the dielectric substrate 102 is exposed to an incident time varying electric field 106 that induces an electric field 106' that energizes the microplasma 108.

A gap layer 110 is positioned or formed on the inner surface 112 of the dielectric substrate 102. The gap layer 110 may be formed of the same material as the dielectric substrate 102 or may be formed of a different material. In some embodiments, the gap layer 110 is formed directly in the dielectric substrate 102 or is otherwise integral with the dielectric substrate 102. The thickness 114 of the gap layer 110 is chosen to be the desired spacing between the dielectric substrate 102 and the shield 116. For example, in some embodiments, the thickness 114 of the gap layer 110 is in the range of 0.001 to 0.060 in.

The gap layer 110 physically separates the dielectric substrate 102 from the shield 116. The gap layer 110 can also provide a mechanical connection between the dielectric substrate 102 and the shield 116. The gap layer 110 connects the dielectric substrate 102 and the shield 116 at locations of sufficient regularity to mechanically stabilize the shield 116 and to maintain the relative alignment of the shield 116 to the dielectric substrate 102.

A relief structure 118 is formed in the gap layer 110 at a predetermined location. The term "relief structure" is defined herein to mean a physical structure that reduces or eliminates the formation of a continuous lateral layer across a structure when the structure is exposed to an incident flux of depositing species. A relief structure, as defined herein, can be formed in a continuous gap layer 110 or a discontinuous gap layer. The relief structure 118 is oriented so that the long dimension of the relief structure 118 (into the page) is positioned such that it includes a component that is perpendicular to the direction of the induced time varying electric field 106'. In some embodiments, the component is not perfectly perpendicular.

The relief structure 118 shown in FIG. 1 has a depth that is equal to the depth 114 of the gap layer 110. However, in some embodiments of the present invention, the depth 114 of the relief structure 118 is less than or greater than the depth of the gap layer 110. In some embodiments, the relief structure 110 is undercut relative to the shield 116 by a lateral distance that is greater than 10% of the thickness 114 of the gap layer 110.

The shield 116 is positioned adjacent to the gap layer 110. The shield 116 should be formed of a material that is resistant to erosion and to decomposition resulting from exposure to the microplasma because the shield 116 is exposed directly to the microplasma 108. In many embodiments, the shield 116 is formed of a metallic material. However, the shield 116 can also be formed of numerous non-metallic materials.

The shield 116 includes a slit 120 having a slit width 122 that is aligned over the relief structure 118 in the gap layer 110. The direction of the slit 120 is oriented so that the long dimension of the slit 120 (into the page) is positioned with a component that is perpendicular to a direction of the induced time varying electric field 106' in the microplasma 108. The dimensions of the slit 120 and the relief structure 118 including the gap thickness 114 are chosen so that the gap layer 110 provides the necessary mechanical rigidity and support. In some embodiments, a shield 116 having a relatively high fraction of open slit area can be used if the dimensions of the relief structure 118 are properly chosen.

The shield 116 can be formed in numerous ways. In many embodiments, the shield 116 is deposited on the gap layer 110 using microfabrication techniques known in the art. For example, the desired shield area can be patterned using photolithographic techniques and the shield material can be deposited using electron beam evaporation, sputtering, or plating techniques that are known in the art. In another embodiment, the shield 116 is bonded or otherwise attached to the gap layer 110 material.

FIG. 1 shows a coating material 124 that is formed on top of the shield 116. The coating material 124 is deposited on the shield 116 and in the bottom of the relief structure 118 because the shield 116 is exposed to the microplasma 108. The coating material 124 is undesirable and is not part of the microplasma source 100. The coating material 124 is deposited during normal operation of the microplasma source over a period of time. The particular operating environment determines the thickness and composition of the coating material.

The coating material 124 shown in FIG. 1 is merely a representative example a possible layer of coating material 124 that can be deposited during the normal operation of the microplasma source 100. A continuous coating layer across the slit 120 in the shield 116 would provide a current carrying path that prevents inductive fields from reaching the plasma region in the chamber, thereby rendering the microplasma source 100 inoperative. Such a continuous coating would require either that the microplasma source 100 to be cleaned in some manner to remove the coating, or that it be replaced with a new source. Cleaning the microplasma source 100 may not always be practical and replacement may incur undesirable or intolerable cost.

Some shields according to the present invention will not prevent the formation of a continuous coating that renders the microplasma source inoperative for an extended operating period. However, these shields will significantly prolong the lifetime of the microplasma source or the required time between cleaning the microplasma source 100.

The slit 120 and relief structure 118 are designed to have dimension that prevent the coating material 124 from forming a continuous film across the shield 116. The thickness 114 of the gap layer 110 and the slit width 122 in the shield 116 are chosen so that the coating material 124 can be deposited through the slit 120 and into the predetermined area of the gap layer 110 without forming a continuous coating layer across the slit 120 in the shield 116.

One embodiment of the microplasma source of the present invention includes an antenna structure 126 that is positioned proximate to the outer surface 104 of the dielectric substrate 102. The antenna structure 126 comprises at least one electrode that generates the incident time varying electromagnetic field 106 when current is flowing through the electrode. The incident time varying electric field 106 generates an induced electric field 106' into the plasma chamber. The electrode is formed of a metal, such as Cu, Au, Al, Au, Ag, Pt, TiW. One skilled in the art will appreciate that many different types of antenna structures 126 can be used in the microplasma source of the present invention. In many embodiments, the antenna structure 126 is a planar electrode structure, such as a loop or spiral. The spiral can be any type of spiral geometry, such as a circular spiral or a square shaped spiral.

The antenna structure 126 is typically operated in a resonant mode in order to minimize antenna losses and to maximize coupling to the plasma inductance. Minimizing parasitic capacitance is important to ensure that energy storage from the RF generator is concentrated in elements (the antenna) which couple to the plasma. In particular, parasitic capacitance-to-ground must be reduced or ideally eliminated.

In one embodiment, the shield 116 is fabricated of conductive material. In this embodiment, the shield 116 can be capacitively coupled to the antenna structure 126 and can also be coupled to ground. Such a shield 116 provides the antenna structure 126 a low impedance path to ground, which would substantially modify the electrical parameters of the antenna structure 126 and reduce coupling to the microplasma.

An output of a RF generator 128 is coupled to the antenna structure 126. Numerous types of RF generators can be used. For example, the RF generator 128 can be a commercially available RF power amplifier chip that consumes only a few watts of total power and that can be used to generate relatively small and highly efficient plasmas in the chamber. A microplasma source according to the present invention using such a RF generator has relatively low power dissipation and does not require cooling.

In one embodiment, an impedance matching network 130 is used to match the output impedance of the RF generator 128 to the impedance seen at the input of the antenna structure 126. The impedance matching network 130 is shown schematically in FIG. 1. However, an impedance matching network according to the present invention can be monolithically integrated into the outer surface 104 of the dielectric substrate 102 or may be realized in a hybrid construction. The impedance matching network 130 can vary impedance element and/or can vary the drive frequency in order to obtain an impedance match. One skilled in the art will realize that many impedance matching network configurations are possible.

Other embodiments of the microplasma source of the present invention do not use antenna structures. Instead, an incident electromagnetic wave having an incident electromagnetic field is propagated proximate to the outer surface 104 of the dielectric substrate 102 so as to generate an induced electric field 106' in the plasma chamber.

In one embodiment, a magnet is positioned proximate to the outer surface 104 of the dielectric substrate 102. The magnet generates a magnetic field for confining the microplasma 108 generated by the microplasma source 100. It may additionally act to allow a cyclotron resonance coupling to be achieved.

FIG. 2 illustrates cross sectional views of other embodiments of a single slit of a shielded microplasma source according to the present invention. The relief structure 118 in the single slit cross section of the shielded microplasma source shown in FIG. 1 has V shaped sidewall. One skilled in the art will appreciate that the relief structure 118 can include many different sidewall shapes as long as the sidewall shape prevent the formation of a continuous conducting film across the slit 120.

Figure 2A:
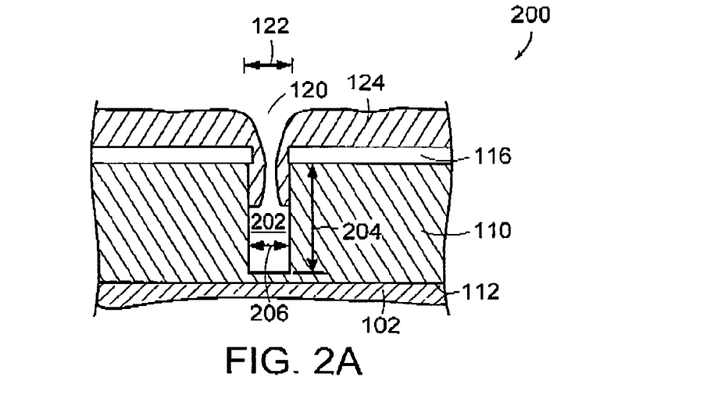
FIG. 2 illustrates cross sectional views of other embodiments of a single slit of a shielded microplasma source according to the present invention.

FIG. 2A illustrates an alternative cross sectional view of a single slit of a shielded microplasma source 200 according to the present invention. The microplasma source 200 includes a relief structure 202 that forms a high-aspect-ratio trench. The width 122 of the slit 120 in the shield 116 and the depth 204 of the relief structure 202 are chosen so that the coating material 124 does not pinch off the relief structure 202 and form a continuous film during deposition. In one embodiment, the depth 204 of the relief structure 202 is chosen to be sufficient to prevent deposition on the bottom of the relief structure 202.

A high-aspect ratio relief structure 202 where the depth 204 of the relief structure 202 is greater than about twice the width 206 of the relief structure 202 is desirable when the plasma contains depositing flux that has a relatively low surface mobility. Using a high-aspect-ratio relief structure 202 will limit the rate at which material in the depositing flux reaches the extremity of the relief structure 202.

Figure 2B:
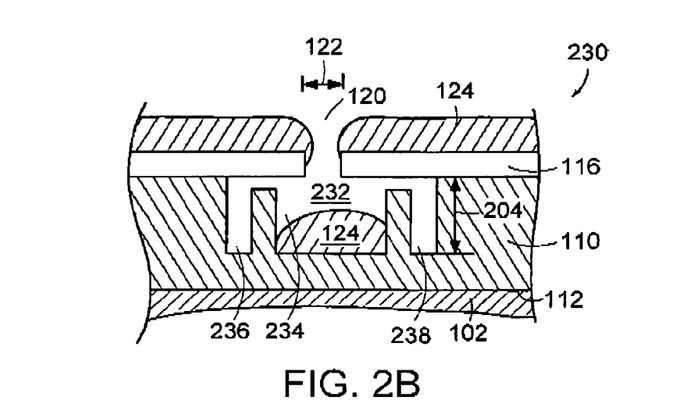

FIG. 2B illustrates an alternative cross sectional view of a single slit of a shielded microplasma source 230 according to the present invention. The microplasma source 230 includes a relief structure 232 that forms three high-aspect-ratio trenches. A relatively large high-aspect-ratio trench 234 is aligned with the slit 120. Two smaller high-aspect-ratio trenches 236, 238 are positioned adjacent to each side of the larger high-aspect-ratio trench 234.

The relief structure 232 shown in FIG. 2B results in convolutions that greatly increase the surface path length between the two sides of the slit 120. Such a relief structure 232 will be more resistant to deposition materials from the microplasma when high surface mobility depositing flux is present in the microplasma. One skilled in the art will appreciate that there are many alternative relief structure geometries that will increase the path length and improve the performance of the microplasma source of the present invention.

In other similar embodiments, the relief structure 232 has one sidewall that is perpendicular to the inner surface 112 of the dielectric substrate 102 and one sidewall that forms an acute angle with the inner surface 112 of the dielectric substrate 102 as shown in the relief structure of FIG. 1. The width 122 of the slit 120 and the depth 204 of the relief structure 232 are chosen so that the coating material 124 does not pinch off the relief structure 232 and form a continuous film.

In yet other embodiments, the microplasma source of the present invention includes a relief structure that is undercut, such as the relief structure 118 shown in FIG. 1. An undercut relief structure is desirable when the plasma contains depositing flux that is highly directional. For example, if the majority species in the plasma is ionized and accelerated across a plasma sheath, an undercut relief structure will significantly help to prevent deposition under the lip of the relief structure 118. If the depositing flux in the plasma is highly directional only a minimal lip would be required. If the depositing flux in the plasma has a very high surface mobility, a highly convoluted structure might be required.

Figure 2C:
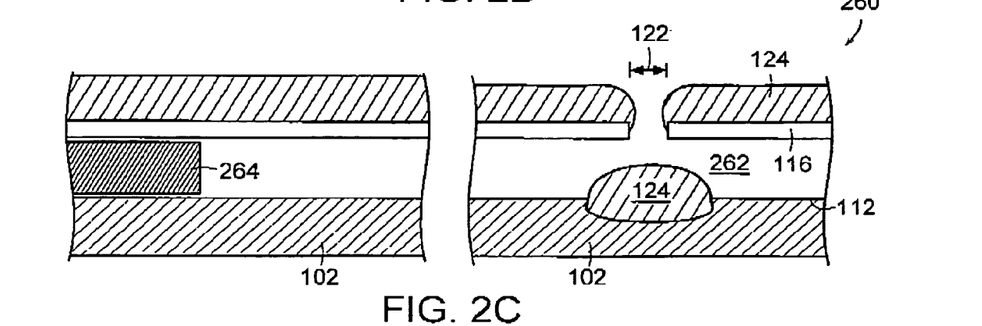

FIG. 2C illustrates an alternative cross sectional view of a single slit of a shielded microplasma source 260 according to the present invention. The microplasma source 260 includes a relief structure 262 that includes a space between the shield and dielectric substrate that is maintained by the physical assembly of two components. In one embodiment a spacer 264 is used to separate the dielectric substrate 102 from the shield 116.

The relief structure 118, 202, 232, 262 can be formed by the gap layer 110 and the shield 116 in numerous ways that are known in the art. For example, the relief structure can be formed using a removal processes, such as chemical etching and/or physically erosion. In particular, the relief structure can be formed using ion bombardment, reactive ion etching, electrical discharge, or one of numerous other machining processes. The relief structure can also be formed using a build-up process, such as electro deposition and selective plating. In addition, the relief structure can be formed by stamping or by other deformation processes. The shield 116 can be formed in numerous ways. For example, the shield 116 can be formed by using microfabrication techniques, such as photolithography and lift-off techniques.

Figure 3:
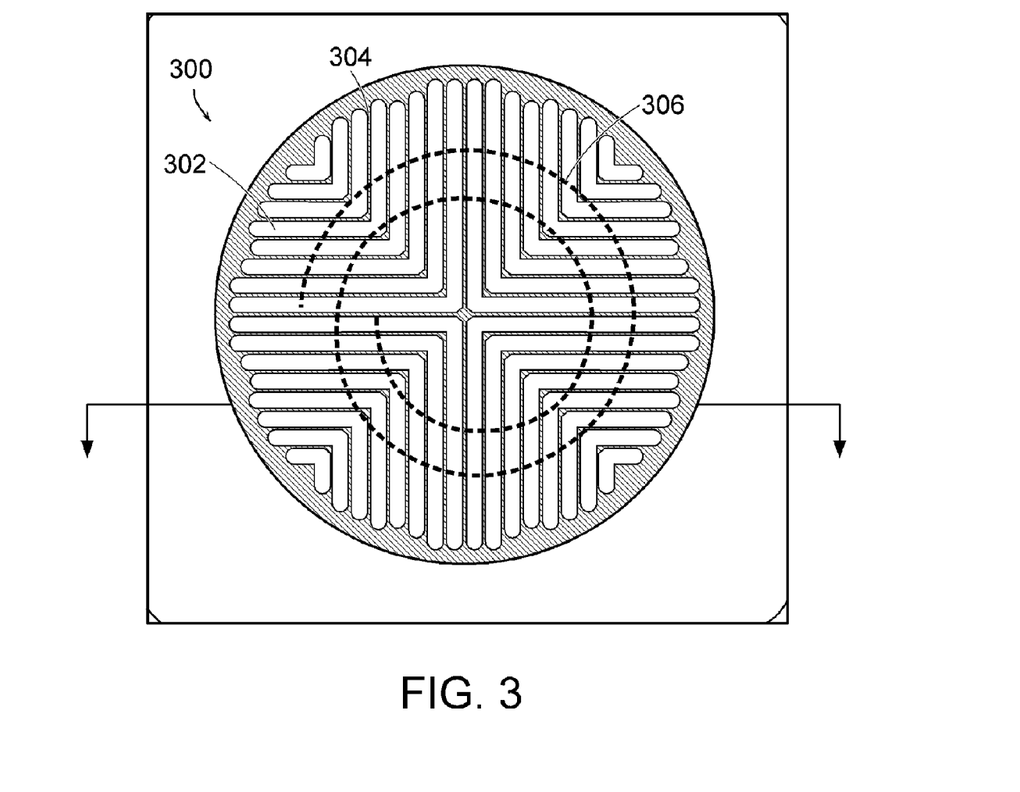
FIG. 3 illustrates a top-view of an embodiment of a microplasma source that includes a shield with a plurality of slits and a plurality of relief structures according to the present invention.

FIG. 3 illustrates a top-view of an embodiment of a microplasma source 300 that includes a shield 302 having a plurality of slits 304 according to the present invention. In many practical embodiments, the microplasma sources of FIGS. 1 and 2 include a shield with a plurality of slits. A cross section line is shown in FIG. 3 to indicate the plane in which the cross section views of a single slit illustrated in FIGS. 1 and 2 are obtained. One skilled in the art will appreciate that the plurality of slits 304 shown in FIG. 3 can be configured in numerous ways.

A spiral antenna 306 is shown as a dotted line to indicate that it is located on or in close proximity to the outer surface 104 (FIG. 1) of the dielectric substrate 102 that is opposite to the plurality of slits 304. In one embodiment, the spiral antenna 306 has a radius that is in the range of 1 to 10 cm. In one embodiment, the plurality of slits 304 is configured so that the slits are aligned mostly perpendicular to the direction of current flow in the spiral antenna 306. The direction of current flow in the spiral antenna 306 is parallel to the direction of the incident time varying electric field 106 shown in FIG. 1.

In some embodiments, at least one slit in the plurality of slits 304 is aligned in a substantially perpendicular direction with respect to the current flow in the spiral antenna 306. In this embodiment, other slits can be aligned in a direction that is substantially parallel to the direction of the current flow in the spiral antenna 306. Those skilled in the art will appreciate that there are many possible slit and antenna configurations and many possible orientations between the slits and the antenna.

Figure 4A:
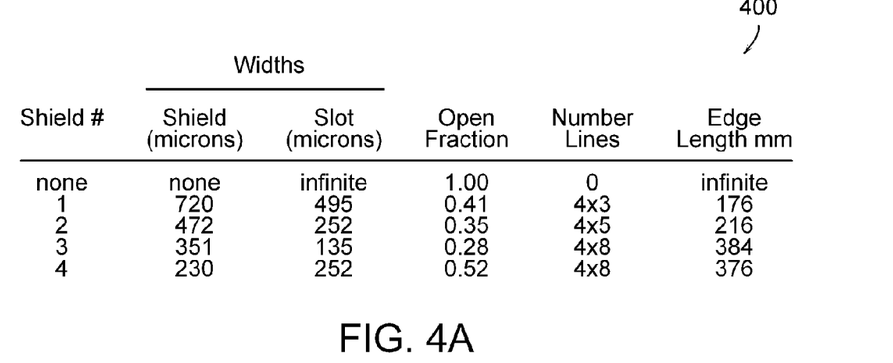
FIG. 4A illustrates a table including dimension of microplasma sources that have been constructed according to the present invention.

FIG. 4A illustrates a table 400 including dimension of microplasma sources that have been constructed according to the present invention. The table 400 includes the shield width, the slot width, the open area fraction, the number of lines and the edge length. The term "edge length" is defined herein as the dimension along the long axis of the slit, summed over all slits in the microplasma source. The term "open area fraction" is defined herein as the total area of the slits relative to the total area of the microplasma source. Thus, the open area fraction is an open area fill factor. A high open area fraction is obtained when the lateral dimension of the shields is small relative to the slit width.

Shielded microplasma sources having open area fractions that are in the range of 20 to 50% have been fabricated with the dimensions indicated in the table. In this example, the dimensions of the shield are relatively small and may not be mechanically stable as freestanding structures. However, integrating these shields in the microplasma source of the present invention adds significant mechanically stability. The increased mechanical stability allows antenna structure designs that have open area fractions that are greater than 50% assuming that the slit 120 and shield 116 dimensions are properly chosen.

Figure 4B:
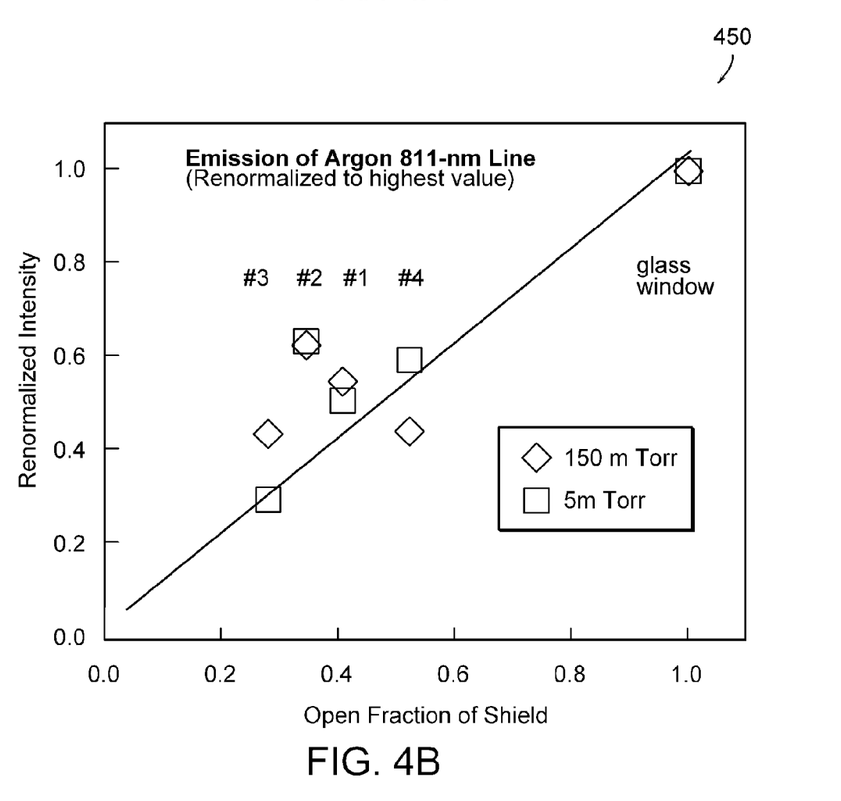
FIG. 4B illustrates a graph of normalized intensity as a function of open area fraction for the microplasma sources listed in FIG. 4A.

FIG. 4B illustrates a graph 450 of normalized intensity as a function of open area fraction for the microplasma sources listed in FIG. 4A. Data is presented for both 150 mTorr and 5 mTorr operating pressure. Several important design considerations for shielded microplasmas are illustrated in FIG. 4B.

The open area fraction is an important parameter. Microplasma source number 3 and microplasma source number 4 have identical numbers of shield lines, but different line and gap widths, so their open area fractions are different. The data in FIG. 4B indicates that a higher open area fraction results in a higher intensity. The effect of pressure is also important to the design parameters. Data taken at a 5 mTorr pressure indicates operation deep in the microplasma regime defined herein (Rp<<ωLp), and a relatively large sheath to plasma volume ratio, Rsp.

Higher open area fractions are desirable in some embodiments because these microplasma sources have relatively high efficiency because of their relatively high coupling. Open area fractions greater than 50% can be achieved. In addition, a relatively high number of slits is desirable in some embodiments because increasing the number of slits will generally increase the coupling efficiency. For example, microplasma source number 2 has improved performance relative to microplasma source number 1, even though its open area fraction is lower. The improved performance is due at least in part to a higher number of slits.

Increasing the coupling efficiency in a microplasma sources is generally desirable because microplasmas have relatively low coupling efficiency compared with conventional plasmas. The relatively low coupling efficiency is caused by the relatively low impedance, $R_p$, and the relatively low effective inductance of the plasma. Conventional plasmas typically operate in the limit of $R_p<<\omega L_p$, whereas microplasmas typically operate in the limit of $R_p>>\omega_p$. Thus, microplasmas have significantly higher antenna losses compared with conventional inductively coupled plasmas. In addition, microplasmas have significantly lower coupling efficiencies compared with conventional inductively coupled plasmas (~10% for microplasmas relative to ~90% for conventional plasmas). See for example, Hopwood J. Vac. Sci. Technol. B 18.5, September/October 2000 pg. 2446.

In one embodiment, the shielded microplasma source of the present invention is used for plasma emission spectrometry. Plasma emission spectrometry is a common analytical technique used to analyze materials introduced into a gas phase. Many industrial and scientific applications require gas phase analysis of materials. Also, many environmental applications require gas phase analysis of materials to obtain data useful for health and safety analysis.

Plasma emission spectrometry is performed by electrically exciting gas to form a plasma where one or more species undergo excitation and decay via emission at UV, visible, or infrared wavelengths. The gas composition or the composition of liquid phase analytes that are volatilized into a gas stream can be determined by a detailed spectral analysis of these emissions. The spectral analysis can include ultraviolet and infrared spectral analysis depending upon the particular application. In many cases the environment in which the microplasma emission spectrometer is operating may include gases or analytes which deposit on interior surfaces.

An emission spectrometer system with advanced capabilities can be constructed from the shielded microplasma source of the present invention. Ultraviolet to near infrared emission spectrometry can be achieved with such a system. Microplasma sources are useful for portable and small emission spectrometers. See for example, U.S. patent application Ser. No. 10/708,450, entitled "Microplasma Emission Spectrometer", filed Mar. 4, 2004, which is assigned to the present assignee. The entire disclosure of U.S. patent application Ser. No. 10/708,450 is incorporated herein by reference.

Figure 5:
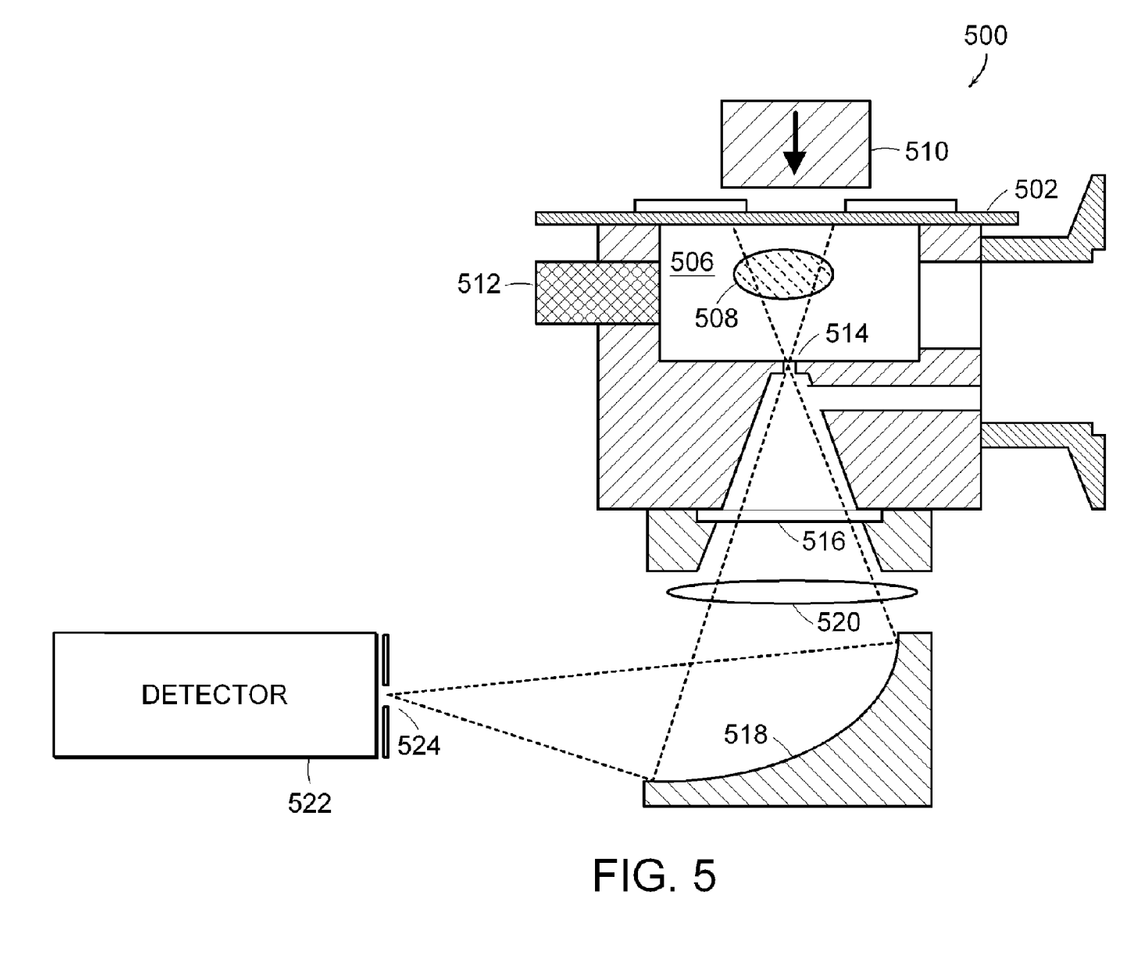
FIG. 5 is a block diagram of a cross sectional view of a microplasma emission spectrometer that includes the microplasma source of the present invention.

FIG. 5 is a block diagram of a cross sectional view of a microplasma emission spectrometer 500 that includes the microplasma source of the present invention. The microplasma emission spectrometer 500 includes a microplasma source 502, such as the microplasma source 100 that was described in connection with FIG. 1. The outer surface of the microplasma source 502 is exposed to a time varying electric field or includes an antenna structure that is positioned on or proximate to the microplasma source 502. The antenna structure induces an electric field into the chamber 506 that generates a microplasma 508.

The chamber 506 is designed to contain a volume of gas for analysis and the microplasma 508 that is formed from the volume of gas. The chamber 506 includes a gas inlet port through which a gas sample may enter. More than one port may be used to provide flow through the chamber 506. In some embodiments, the chamber 506 is coupled to a vacuum pump that evacuates the chamber 506 so that the chamber 506 can be maintained at a sub-atmospheric pressure level in order to facilitate the introduction of the volume of gas for analysis.

In one embodiment, the microplasma emission spectrometer 500 includes a magnet 510 that is positioned adjacent to the outer surface of the microplasma source 502. The magnet 510 can be any type of magnet, such as a permanent magnet or an electromagnet. The magnet 510 generates a magnetic field for confining the microplasma 508 that is generated by the microplasma source 502 and may enhance coupling through cyclotron resonance.

A plasma igniter 512, such as an ignition electrode that generates an arc or electron spray into the chamber 506 or an UV radiation source that introduces UV radiation into the chamber 506, can be used to initially ignite the microplasma 508.

Pressure control in the chamber 506 can also be provided by a system (not shown) interfacing with the microplasma spectrometer 500. The chamber 506 can be isolated using valves so that the gas sample is completely confined, or may be capable of gas exchange through diffusion, conduction or convective mechanisms. In the embodiment shown, the chamber 506 connects to a tubulation and connecting fitting.

The chamber 506 includes an exit aperture 514 that provides an outlet for emissions from the microplasma 508 generated in the chamber 506. In one embodiment, the exit aperture 514 is formed in a transmission window 516 that comprises the bottom of the chamber 506. In another embodiment, the exit aperture 514 is a separate element, such as a thin piece of foil, which is placed or attached to the bottom of the chamber 506. In another embodiment, the exit aperture 514 is machined directly into the chamber 506.

In yet another embodiment, the exit aperture 514 has a small open area that is remotely positioned relative to the transmission window 516. The small open area can reduce undesirable depositions on the transmission window 516. Increasing the spacing between the exit aperture 514 and the transmission window 516 will reduce the deposition rate at the transmission window 516. It is desirable to have the spacing be larger than a mean free path because the probability of scattering to a wall is increased. In one embodiment, deposition is decreased by using a high ratio of window area to exit aperture area. For example, a ratio of window area to exit aperture area that is equal to about ten will decrease the deposition rate by a factor of ten. The combination of the shielded microplasma with these features makes the microplasma emission spectrometer according to the present invention immune to, or resistant to, the deposition of coating materials.

In one embodiment, the exit aperture 514 and transmission window 516 are dimensioned and positioned so that the combination subtends a large fraction of the microplasma 508 in order to maximize the optical emission flux that is imaged or transmitted through the transmission window 516. Maximizing the optical emission flux will improve the efficiency of the microplasma emission spectrometer 500.

The particular geometry of the exit aperture 514 that maximizes optical intensity depends upon the particular geometry of the resonant antenna structure of the microplasma source 500. The geometry of the exit aperture 514 that maximizes the optical emission flux from the microplasma source 500 can be a plane, a line, or a circle.

For example, a microplasma spectrometer has been constructed having an exit aperture forming a slit that is oriented perpendicular to a plane of a coil shaped antenna structure with the center point of the slit positioned in close proximity (2-5 mm) to the surface of the antenna structure. Experiments have shown that such an exit aperture passed a 50% larger portion of the optical emission flux from the microplasma 508 than an exit aperture that is oriented parallel to the plane because the emission intensity was concentrated in a thin disk parallel to the antenna.

An optical transmission window 516 is positioned adjacent to the exit aperture 514 in the optical path of the optical emission flux from the microplasma 508. Collection optics 518 are positioned adjacent to the optical transmission window 516 in the optical path of the emission flux from the microplasma source 500. The collection optics 518 may include an additional lens 520 that focuses the emission flux.

The collection optics 518 are used for collecting, refocusing, and transmitting the optical emission flux from the microplasma 508 to an entrance aperture 524 or focal plane of a spectrally sensitive detection system 522. The exit aperture 514, transmission window 516, and collection optics 518 together limit the portion of the plasma volume from which emissions may be collected.

For example, in one embodiment, the diameter of the transmission window 516 is about 0.5 cm and the exit aperture 514 is configured as a narrow slit having a width that is about 0.5 mm and a height that is about 2.5 mm. The transmission window 516 is located approximately 1 cm from the exit aperture 514. The center of the chamber 506 and the microplasma 508 are spaced a distance that is about 1 cm from the exit aperture 514. The resulting microplasma is approximately a cube with sides of length 1 cm. Ray-tracing methods can be used to calculate the fraction of the microplasma from which optical emission may be imaged or transmitted to the detector. In this example, the fraction is approximately one-eighth of the microplasma volume.

In another embodiment, the exit aperture 514, transmission window 516 and collection optics 518 are chosen so that emissions from at least one-quarter of a total volume of the microplasma 508 are imaged or transmitted through the entrance aperture 524 of a spectrally sensitive detection system 522. In yet other embodiments, emissions from at least one-half of a total volume of the microplasma are imaged or transmitted through the entrance aperture 524 of a spectrally sensitive detection system 522.

In one embodiment, the entrance aperture 524 of the spectrally sensitive optical detection system 522 is butt-coupled to the exit aperture 514 of the chamber 506. In this embodiment, the microplasma subtends substantially the entire acceptance cone of the entrance aperture 524. The dimensions of the exit aperture 514 are chosen so that they do not substantially limit the emissions accepted by the spectrally sensitive detection system 522.

The spectrally sensitive detection system 522 can be any of numerous types of optical detection systems. For example, the spectrally sensitive optical detection system 522 can be a spectrometer, a detector array, a monochromator based spectrometer, or one or more single wavelength detectors, such as a filter and photodiode.

The microplasma source of the present invention consumes relatively little power, allowing the power supply, plasma source 500, and spectrally sensitive detector 522 to be in close proximity in a miniaturized package. Maintaining a relatively low temperature at the spectrally sensitive detector 522 is desirable to limit thermal noise. In one embodiment, the microplasma source 500 is thermally isolated from the spectrally sensitive detector 522. In another embodiment the spectrally sensitive detector 522 is actively cooled. In some embodiments less than 20 W are consumed by the plasma source 502, allowing the use of passive cooling.

In one embodiment, the spectrally sensitive optical detection system 522 is a spectrometer. The entrance aperture 524 can be the entrance slit of the spectrometer and the chamber 506 can be directly integrated into the spectrometer. The entrance aperture 524 dimensions can be chosen to optimize spectrometer performance based upon resolution and throughput. In one embodiment, the width of the exit aperture 514 is slightly wider than the entrance slit of the spectrometer so as to simplify alignment of the microplasma source 500 to the spectrometer. The chamber 506 is temperature controlled in some embodiments in order to maintain optical alignment tolerances and/or to reduce coating of the interior surfaces.

EQUIVALENTS

While the present teachings are described in conjunction with various embodiments and examples, it is not intended that the present teachings be limited to such embodiments. On the contrary, the present teachings encompass various alternatives, modifications and equivalents, as will be appreciated by those of skill in the art, may be made therein without departing from the spirit and scope of the invention as defined by the appended claims.

What is claimed is:

1. A microplasma source comprising:
   a) a dielectric substrate;
   b) a gap layer that is positioned proximate to an inner surface of the dielectric substrate;
   c) a shield that is positioned on the gap layer, the shield comprising at least one slit positioned parallel to the inner surface of the dielectric substrate;
   d) an antenna structure that is positioned parallel to an outer surface of the dielectric substrate, the antenna structure generating a time varying electric field parallel to the inner surface of the dielectric substrate;
   e) a chamber being positioned adjacent to the shield, wherein a gas in the chamber being ionized to form a microplasma having a plasma sheath volume-to-total plasma volume ratio greater than 0.01 when an electromagnetic field is induced in the chamber by the incident time varying electric field; and
   f) a relief structure formed from the inner surfaces of the dielectric substrate, the gap layer, and the slit, the relief structure preventing depositing species incident from the chamber from forming continuous coatings with finite conductivity across a profile of the relief structure.

2. The microplasma source of claim 1 wherein the dielectric substrate and the gap layer comprise the same material.

3. The microplasma source of claim 1 wherein the dielectric substrate and the gap layer are monolithically integrated.

4. The microplasma source of claim 1 wherein the gap layer and shield are monolithically integrated.

5. The microplasma source of claim 1 wherein the relief structure comprises at least one sidewall that is oriented perpendicular to the inner surface of the dielectric substrate.

6. The microplasma source of claim 1 wherein the relief structure comprises at least one sidewall that forms an acute angle with the inner surface of the dielectric substrate.

7. The microplasma source of claim 1 wherein a depth of the relief structure is greater than a thickness of the gap layer.

8. The microplasma source of claim 1 wherein the relief structure is undercut with respect to the shield by a lateral distance that is greater than 10% of a thickness of the gap layer.

9. The microplasma source of claim 1 wherein an open area fraction of the shield is in the range of 10-90%.

10. The microplasma source of claim 1 further comprising an antenna structure that is positioned proximate to the outer surface of the dielectric substrate.

11. The microplasma source of claim 10 wherein the antenna structure comprises a spiral inductive antenna structure.

12. The microplasma source of claim 10 wherein the antenna structure comprises a resonant antenna structure.

13. The microplasma source of claim 10 wherein the antenna structure is monolithically integrated into the outer surface of the dielectric substrate.

14. The microplasma source of claim 1 further comprising a RF generator that generates the incident time varying electric field.

15. The microplasma source of claim 14 further comprising an impedance matching network that matches an output impedance of the RF generator to an impedance seen at an input of the antenna structure.

16. The microplasma source of claim 15 wherein the impedance matching network is formed on the dielectric substrate.

17. A monolithic microplasma source comprising:
a) a dielectric substrate;
b) a gap layer that is positioned proximate to an inner surface of the dielectric substrate;
c) a shield that is positioned proximate to the gap layer, the shield comprising a plurality of slits positioned parallel to the inner surface of the dielectric substrate;
d) an antenna structure that is positioned parallel to an outer surface of the dielectric substrate, the antenna structure generating a time varying electric field parallel to the inner surface of the dielectric substrate;
e) a plurality of relief structures that are formed in at least one of the gap layer and the dielectric substrate, at least one of the gap layer, the plurality of slits, and the plurality of relief structures preventing a formation of a continuous film across the plurality of relief structures; and
f) a chamber being positioned adjacent to the shield, wherein a gas in the chamber being ionized to form a microplasma having a plasma sheath volume-to-total plasma volume ratio greater than 0.01 when an electromagnetic field is induced in the chamber.

18. The microplasma source of claim 17 wherein at least one of the plurality of relief structures comprises at least one sidewall that is perpendicular to the inner surface of the dielectric substrate.

19. The microplasma source of claim 17 wherein at least one of the plurality of relief structures comprises at least one sidewall that forms an acute angle with the inner surface of the dielectric substrate.

20. The microplasma source of claim 17 wherein a depth of at least one of the plurality of relief structures is greater than a thickness of the gap layer.

21. The microplasma source of claim 17 wherein at least one of the plurality of relief structures is undercut with respect to a respective one of the plurality of slits by a lateral distance that is greater than 10% of a thickness of the gap layer.

22. The microplasma source of claim 17 wherein an open area fraction is in the range of 10-90%.

23. The microplasma source of claim 17 further comprising an antenna structure that is monolithically integrated into an outer surface of the dielectric substrate.

24. The microplasma source of claim 17 further comprising a RF generator that generates an incident time varying electric field that induces the electric field into the chamber.

25. The microplasma source of claim 24 further comprising an impedance matching network that matches an output impedance of the RF generator to an impedance seen at an input of the antenna structure.

26. The microplasma source of claim 25 wherein the impedance matching network is monolithically integrated into the dielectric substrate.

27. A microplasma source comprising:
a) a dielectric substrate having an outer surface that is exposed to a time varying electric field;
b) a chamber being positioned adjacent to an inner surface of the dielectric substrate, wherein a gas in the chamber being is ionized to form a microplasma having a plasma sheath volume-to-total plasma volume ratio greater than 0.01 when an electromagnetic field is induced in the chamber by the incident electric field;
c) means for radiating a time varying electric field parallel to the inner surface of the dielectric substrate;
d) a means for shielding a portion of the dielectric substrate; and
e) a means for preventing a formation of a continuous film of material across the inner surface of the dielectric substrate.

* * * * *